US00PP11900P2

(12) United States Plant Patent
Morrison

(10) Patent No.: US PP11,900 P2
(45) Date of Patent: Jun. 5, 2001

(54) HIBISCUS PLANT NAMED 'PLANT NO. 179'

(75) Inventor: William L. Morrison, Park Ridge, IL (US)

(73) Assignee: Gilberg Perennial Farms, Inc., Glencoe, MO (US)

( * ) Notice: Subject to any disclaimer, the term of this patent is extended or adjusted under 35 U.S.C. 154(b) by 0 days.

(21) Appl. No.: 09/324,082

(22) Filed: Jun. 1, 1999

(51) Int. Cl.[7] ..... A01H 5/00
(52) U.S. Cl. ..... Plt./257
(58) Field of Search ..... Plt./257

(56) References Cited

U.S. PATENT DOCUMENTS

P.P. 11,165 * 12/1999 Morrison ..... Plt./257
P.P. 11,166 * 12/1999 Morrison ..... Plt./257

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Hibiscus plant named 'Plant No. 179', characterized by its plant height of about 3.5 to 5.5 feet; very large flat flowers with fully overlapping petals; vibrant pink flower color; flowers that maintain their flat shape for up to two days; long flowering period; resistance to diseases and insects common to Hibiscus; tolerance to humidity exremes; tolerance to drought and flooding; and tolerance to temperatures extremes.

1 Drawing Sheet

BACKGROUND OF THE INVENTION

The present invention relates to a new and distinct cultivar of winter-hardy Hibiscus, or Rose Mallow, botanically known as *Hibiscus moscheutos*, and hereinafter referred to by the cultivar name 'Plant No. 179'.

The new cultivar is a product of a planned breeding program conducted by the Inventor in Park Ridge, Ill. The objective of the breeding program is to create new Hibiscus cultivars having large flat flowers with overlapping petals, long-lasting flowers, long flowering period and attractive flower colors.

The new cultivar originated from a cross made by the Inventor in Park Ridge, Ill., of the nonpatented *Hibiscus moscheutos* cultivar 'Red Plate', as the female, or seed, parent with the nonpatented *Hibiscus moscheutos* cultivar 'Bills's Giant White' as the male, or pollen, parent.

The cultivar 'Plant No. 179' was discovered and selected by the Inventor as a flowering plant within the progeny of the stated cross in a controlled environment in Park Ridge, Ill. in 1993.

Compared to plants of the male parent, the cultivar 'Bill's Giant White', and the female parent, the cultivar 'Red Plate', plants of the new Hibiscus have larger flowers, flatter flowers, a longer flowering period, maintain the flat flower shape longer and differ in flower color.

Asexual reproduction of the new cultivar by root crown divisions and by terminal and stem cuttings taken in a controlled environment in Park Ridge, Ill., has shown that the unqiue features of this new Hibiscus are stable and reproduced true to type in successive generations.

SUMMARY OF THE INVENTION

The cultivar 'Plant No. 179' has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Plant No. 179'. These characteristics in combination distinguish 'Plant No. 179' as a new and distinct cultivar:

1. Plant height of about 3.5 to 5.5 feet.
2. Very large flat flowers with fully overlapping petals and vibrant pink in color.
3. Flowers that maintain their flat shape for up to two days.
4. Long flowering period.
5. Resistant to diseases and insects common to Hibiscus.
6. Tolerant to humidity extremes.
7. Tolerant to drought and flooding.
8. Tolerant to temperature extremes, plants will tolerate temperature ranges from −25° to 100° F.
9. Roots are not attractive to rodents.

Plants of the new Hibiscus can be compared to plants of the Hibiscus cultivar 'Morrison-Gilberg (IV)', disclosed in U.S. Plant Pat. No. 11,165. In side-by-side comparisons conducted in Pacific, Mo., plants of the new Hibiscus are more rounded in plant shape, have more entire petal margins, more ruffled petals, and more prominent petal veins than plants of the cultivar 'Morrison-Gilberg (IV)'.

BRIEF DESCRIPTION OF THE PHOTGRAPH

The accompanying colored photograph illustrates the overall appearance of the new cultivar, showing the colors as true as it is reasonably possible to obtain in colored reproductions of this type. Colors in the photographs may differ slightly from the color values cited in the detailed botanical description which accurately describe the actual colors of the new Hibiscus. The photograph comprises a close-up view of a typical flower of 'Plant No. 179', developing flower buds and upper and lower leaf surfaces.

DETAILED BOTANICAL DESCRIPTION

The following observations, measurements and values describe plants grown in Park Ridge, Ill. under outdoor conditions with day temperatures ranging from 50 to 100° F. and night temperatures ranging from 45 to 80° F. In the description, color references are made to The Royal Horticultural Society Colour Chart except where general terms of ordinary dictionary significance are used.

Botanical classifications: *Hibiscus moscheutos* cultivar 'Plant No. 179'.

Parentage:

*Female or seed parent.*—*Hibiscus moscheutos* cultivar 'Red Plate', not patented.

*Male or pollen parent.*—*Hibiscus moscheutos* cultivar 'Bill's Giant White', not patented.

Propagation:

*Type.*—By terminal and stem cuttings.

*Time to initiate roots.*—About 7 days.

*Time to develop roots.*—About 14 days.

*Root description.*—Thick and heavy center root crowns; large succulent roots with many fine white secondary roots.

Plant description:

*Plant form.*—Perennial shrub; spherical.

*Plant height, soil level to top of flowers.*—About 4 to 5.5 feet.

*Plant diameter, area of spread.*—About 3.5 to 5.5 feet.

*Internode length.*—About 2 to 5 inches.

*Growth rate.*—Very fast; vigorous. Plants emerge from roots in spring and flower about three to four months later during the summer.

*Lateral branch length.*—About 20 to 40 inches.

*Lateral branch diameter.*—About 0.25 to 0.5 inches.

*Lateral branch texture.*—Smooth.

*Lateral branch color.*—143C.

Foliage description:

*Arrangement.*—Alternate, single.

*Length.*—About 3 to 8 inches.

*Width.*—About 2 to 5 inches.

*Shape.*—Ovate to cordate.

*Apex.*—Acuminate.

*Base.*—Cordate to obtuse.

*Margin.*—Serrate.

*Texture.*—Smooth, glabrous.

*Color.*—Mature foliage, upper surface:139A. Mature foliage, lower surface: 138B.

*Durability to stress.*—Very good.

*Petiole.*—Length: About 3 to 5 inches. Diameter: About 0.125 inches. Color: 143C.

Flower description:

*Flower appearance.*—Very large rounded and flat single flowers with five overlapping petals. Petals vibrant pink in color. Flowers maintain their flat shape for up to two days. As a cut flower, flowers last about one day. Flowers self-cleaning. Not fragrant.

*Time to flower.*—About 90 to 120 days after plants emerge from the root crown in the spring; plants flower for about 20 to 40 days in the midsummer in the Midwestern United States.

*Flower arrangement.*—Flowers arranged singly at terminal leaf axils and face outward.

*Quantity of flowers.*—One year-old plants will produce about five flowers and bus at one time; two year-old plants will produce about 15 flowers and buds at one time; and three year-old plants will produce about 20 flowers and buds at one time.

*Flower diameter.*—*About* 10 to 12 inches.

*Flower bud* (*just before showing color*).—Rate of opening: From visible bud to flower, about four weeks are required depending on temperatures. Length: About 2 to 3.5 inches. Diameter: About 1 to 2 inches. Shape: Ovoid. Color: 60A.

*Petals.*—Arrangement: Corolla consists of five overlapping petals. Length: About 5 to 6 inches. Width: About 5 to 6 inches. Shape: Broadly ovate. Apex: Rounded. Margin: Entire; undulating with some ripples. Texture: Smooth; slightly rippled. Color: Upper surface: 57C with 57D venation. Lower surface: 57D.

*Sepals.*—Number per flower: Five. Length: About 1.5 inches. Width: About 0.75 inches. Shape: Deltoid. Apex: Acute. Color: 143C.

*Peduncles.*—Length: About 3 to 5 inches. Angle: Horizontal. Strength: Strong. Color: 143B.

*Reproductive organs.*—Androecium: Stamen number: About 15 to 25. Anther size: About 0.063 to 0.125 inches. Amount of pollen: Abundant. Pollen color: 162A. Gynoecium: Pistils: One. Pistil length: About 2 to 5 inches. Style color: 155C. Stigma number: Five. Stigma color: 55B. Seed: Capsule length: About 1 inch. Quantity: About 100 seeds per capsule. Length: About 0.125 inches. Diameter: About 0.125 inches. Color: 166B.

Disease/insect resistance: Plants of the new Hibiscus appear to be resistant to known Hibiscus pathogens and insects.

Weather tolerance: Plants of the new Hibiscus are very tolerant to weather extremes including wide ranges in humidity level, drought and flooding. Plants of the new Hibiscus will tolerate temperatures from −25° to 100° F.

It is claimed:

1. A new and distinct Hibiscus plant named 'Plant No. 179', as illustrated and described.

* * * * *

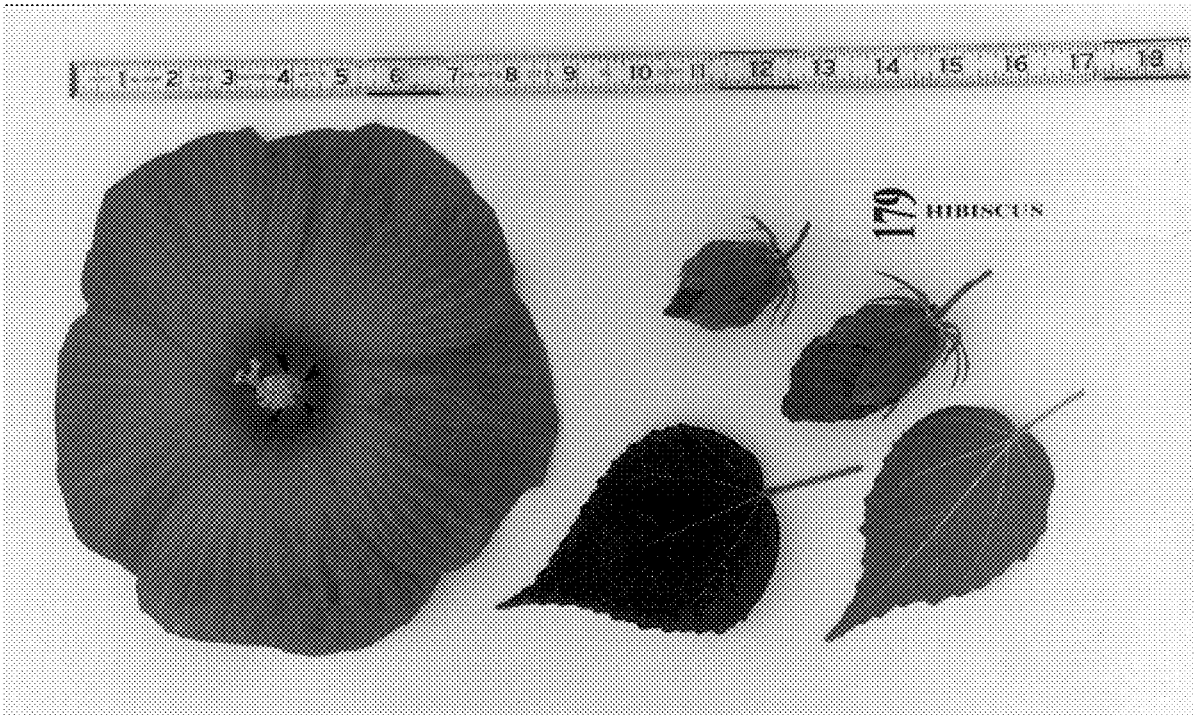
1 2 3 4 5 6 7 8 9 10 11 12 13 14 15 16 17 18
179 HIBISCUS